United States Patent [19]

Zook

[11] Patent Number: 5,497,789
[45] Date of Patent: Mar. 12, 1996

[54] FOOT PROTECTOR INCORPORATING A VISCOELASTIC GEL

[76] Inventor: Gerald P. Zook, 760 E. 29th Ave., Eugene, Oreg. 97405

[21] Appl. No.: 969,530

[22] Filed: Oct. 30, 1992

Related U.S. Application Data

[63] Continuation of Ser. No. 453,150, Dec. 20, 1989, abandoned, which is a continuation-in-part of Ser. No. 273,710, Nov. 17, 1988, abandoned, which is a continuation-in-part of Ser. No. 75,425, Jul. 20, 1987, abandoned.

[51] Int. Cl.⁶ .................................................. A61F 13/06
[52] U.S. Cl. .................................................. 128/893; 128/894
[58] Field of Search ............................... 128/893, 112, 128/113, 117, 593, 894; 602/41

[56] References Cited

U.S. PATENT DOCUMENTS

| | | | |
|---|---|---|---|
| Re. 13,608 | 8/1913 | Rightmire | 128/893 |
| 21,790 | 10/1858 | Wheat | 128/894 |
| 281,487 | 7/1883 | Georges | 128/894 |
| 707,089 | 8/1902 | Duckworth | 128/153 |
| 2,044,523 | 6/1936 | Bertram | 128/153 |
| 2,115,237 | 4/1938 | Scholl | 128/893 |
| 2,585,691 | 2/1952 | Scholl | 128/153 |
| 2,646,795 | 7/1953 | Scholl | 128/153 |
| 2,740,401 | 4/1956 | Crawford | 128/153 |
| 2,781,044 | 2/1957 | Bennett | 128/153 |
| 2,827,049 | 3/1958 | Scholl | 128/153 |
| 2,943,623 | 7/1960 | Thompson | 128/153 |
| 3,209,750 | 10/1965 | Levitt | 128/153 |
| 3,229,690 | 1/1966 | Scholl | 128/153 |
| 3,253,591 | 5/1966 | Scholl | 128/894 |
| 3,487,832 | 1/1970 | Spence | 128/153 |
| 3,547,120 | 12/1970 | Grossman | 128/153 |
| 3,548,420 | 12/1970 | Spence | 3/20 |
| 3,968,530 | 7/1976 | Dyson | 5/449 X |
| 4,369,284 | 1/1983 | Chen | 524/476 |
| 4,380,569 | 4/1983 | Shaw | 428/283 |
| 4,414,964 | 11/1983 | Farino et al. | 128/153 |
| 4,456,642 | 6/1984 | Burgdorfer et al. | 5/449 X |
| 4,516,571 | 5/1985 | Buchan | 128/893 |
| 4,699,146 | 10/1987 | Sieuerding | 128/640 |
| 4,756,949 | 7/1988 | Spence et al. | 428/68 X |
| 4,842,931 | 6/1989 | Zook | 428/354 |

Primary Examiner—Michael A. Brown

[57] ABSTRACT

A padding and medicating device for corns, hammertoes, bunions, blisters, and the like comprising a noncompressible, thermoplastic, oleaginous, viscoelastic gel directly impregnated onto a carrier structure of elastic fabric. The ultrasoft gel is retained on and compressed against the body part being treated by the elastic tension of the fabric which causes the noncompressible gel to expand radially outward, flow over the lesion, and conform to the shape of the lesion in a manner which dissipates externally-applied pressure equally throughout the fabric-gel-tissue system. The invention also internally absorbs frictional or horizontal shearing forces, delivers a therapeutically significant dose of a lubricating, soothing, and emolifying oil such as Mineral Oil U.S.P., and is further capable of delivering a pharmacologically active substance to the foot lesion.

16 Claims, 2 Drawing Sheets

FOOT PROTECTOR INCORPORATING A VISCOELASTIC GEL

REFERENCE TO RELATED APPLICATIONS

This application is a continuation of 07/453,150 filed Dec. 20, 1989, now abandoned, which is a continuation-in-part of Application Ser. No. 273,710 filed Nov. 17, 1988, now abandoned, which is a continuation-in-part of Application Ser. No. 075,425 filed Jul. 20, 1987, now abandoned.

BACKGROUND—FIELD OF INVENTION

This invention relates to foot pads, more specifically to foot pads incorporating a viscoelastic gel with superior friction and pressure-dissipating characteristics as well as medicinal properties.

BACKGROUND—DESCRIPTION OF PRIOR ART

The art of foot padding and medicating devices is old and crowded. Historically, pads for corns, hammertoes, bunions and the like have been manufactured from compressible materials such as felt or foamed latex. This trend continues today as evidenced by the large numbers of such products available on the over-the-counter foot care market.

Wheat in U.S. Pat. No. 21,790 describes a corn eradicator comprising an elastic band and a pad or cushion. Wheat does not disclose what his pad is made of, but most pads of that era were made of fabric such as felt or even softened leather. Wheat shows a relatively narrow elastic band holding the device in place. One disadvantage of a narrow elastic band is that it concentrates pressure on the plantar digital arteries as it loops around the toe. Georges in U.S. Pat. No. 281,487 describes a corn or bunion shield made of discs of soft leather or fabric and a central area of oiled silk to relieve friction. Georges' invention suffers from the following objections: the leather and flannel discs will become compressed and lose their cushioning ability with use, the oiled silk used to relieve friction can leave an oil stain on socks or shoes, the digit encircling elastic band is relatively narrow and thus may impede blood flow in the plantar digital arteries, and the device is not washable and therefore could become unhygenic. Duckworth in U.S. Pat. No. 707,089 teaches a corn pad having an internal cavity to relieve pressure on a corn or bunion and a digit encircling elastic strap. Duckworth's internal cavity would be difficult to manufacture and merely concentrates pressure on the soft tissue surrounding the corn. Again, his narrow elastic band would create pressure on the plantar digital arteries. Schultz in U.S. Pat. No. 893,876 describes a foot protector made of multiple layers of felt or other compressible fabric that may be adjusted by removing one or more layers. Compressible materials such as wool or felt will eventually "bottom out" and loose their ability to cushion. These materials are also poor dissipaters of frictional forces and do nothing to soften and lubricate a keratotic lesion. Patent No. 13,608 to Rightmire teaches a medicating device for cutaneous lesions consisting of one or more medicinal cups affixed to a digit by an elastic tubular carrying structure. The cups are rigid and would create painful pressure points adjacent to the flange structure around the lesion. This device would be of no value in dissipating frictional forces generated by shoe gear. U.S. Pat. No. 2,057,72 to Koppe teaches a corn pad of felt or the like secured to a digit by means of an adhesive strip. This device would not be removable and the felt pad would not be able to absorb frictional forces like a viscoelastic gel would. Scholl in U.S. Pat. No. 2,115,237 teaches a medicated button made of an adhesive plastic mass and incorporating medication. Since the button is made of an adhesive material, it cannot readily be removed and reapplied. Since the plastic mass is composed of relatively stiff materials, it will not dissipate shearing forces as a viscoelastic gel would. U.S. Pat. No. 2,015,497 to Scholl describes a two-component corn plaster with a medicated disc covered with a pressure-relieving corn pad. This device is not removable and reusable and is not made of materials that would dissipate pressure and friction in the "hydraulic" manner as the elastic gel of the present invention. Crawford in U.S. Pat. No. 2,7840,401 teaches a foot-corrective pad made of foamed latex with a central aperture to relieve pressure and a covering of rubber or the like. As with many other prior art references, the foamed latex of Crawford's invention is compressible and when subjected to shoe pressure will become a dense, unyielding material with poor pressure or sheer dissipating properties. A viscoelastic gel, on the other hand, is noncompressible and is capable of dissipating friction and pressure even when subjected to extreme shoe pressure. This fact can be readily demonstrated by taking a corn pad of the present invention, applying firm, or even extreme pressure to the gel pad with a finger, and rubbing to and fro. The finger in this instance will glide almost effortlessly to and fro as the frictional forces are dissipated internally by the gel. The gel will also conform to the contour of the digit to more evenly spread out the pressure exerted upon it from a direction perpendicular to its major surface. This last point means that an aperture, such as described by Crawford, is not a critical feature when utilizing an elastic gel, an important manufacturing consideration. Levitt in U.S. Pat. No. 3,209,750 teaches a digit-embracing surgical pad made of foamed latex which suffers from the same objections as the device taught by Crawford. U.S. Pat. No. 3,244,171 to Neu teaches a surgical pad with a digital loop. This bunion shield is made of compressible materials such as felt or foam rubber and has a large central aperture to relieve pressure and friction. Again, these materials are poorly adapted to dissipate pressure and friction and will bottom out with time. Thompson in U.S. Pat. No. 2,943,623 teaches a skin plaster made of tetrafluroethylene which has a very low coefficient of friction. This device does nothing to pad or soften the keratotic lesion as described in the present invention.

Gelatinous materials are well known to the art of orthopedic cushioning devices. Spence in U.S. Pat. No. 3,548,420 teaches a cushion made with an organosiloxane gel covered by a layer or layers of cloth, foamed plastic or the like. This device has the disadvantage of incorporating a gel without the ability to impart Mineral Oil U.S.P. to a keratotic lesion to soften and lubricate the lesion. Furthermore, the gel in Spence's invention is not elastic enough to dissipate frictional forces when applied in extremely thin layers as described below for the present invention. The same objections hold true for Spence's U.S. Pat. Nos. 3,308,491 and 3,663,973 which teach similar organosiloxane gel devices. Shaw in U.S. Pat. No. 4,380,569 teaches lightweight preformed stable gel structures that incorporate glass microspears. Again, these devices do not bleed Mineral Oil U.S.P. onto a keratotic lesion and lack the elasticity to dissipate friction from shoe gear when employed in extremely thin layers. Burgdorfer et al., in U.S. Pat. No. 4,456,642, teaches gel pads with the same objections as Spence and Shaw.

OBJECTS AND ADVANTAGES

Accordingly, several objects and advantages of my invention are:

(a) To provide a novel pad for corns, calluses, bunions, blisters, and the like which is able to equalize pressure when applied over an uneven surface, such as found with many foot disorders, by utilizing an ultrasoft viscoelastic noncompressible gel which is capable of conforming to the shape of the lesion when pressure is applied and dissipating this pressure in a "hydraulic" manner which spreads this pressure more equally over a larger area than any prior inventions known to this art.

(b) To provide a foot protective and cushioning device which is able to internally absorb frictional or horizontal shearing forces encountered as the foot slides forward and backward inside the shoe during the walking cycle when employed in thinner layers than heretofore known in this art.

(c) To provide a pedal cushioning device which is extremely simple in its design, manufacture, and use. In its simplest form, the present invention is made of only two components, a carrier structure of elastic fabric and a pad of viscoelastic gel which has been impregnated thereupon.

(d) To provide a pad capable of delivering a therapeutically significant amount of skin softening and lubricating oil such as Mineral Oil U.S.P. or a medicinal agent such as keratolytic agent, antifungal, or antibacterial agent, vesicant, or any other pharmacological agent that would be beneficial to the user.

(e) To provide a safe digital cushioning device that is secured to the digit by means of a broad elastic tube rather than a narrow elastic band so that this elastic force is distributed over a wide area so as not to impede circulation to the digit.

(f) To provide a pad for corns, hammertoes, bunions, and the like which is easy to apply and remove, is hand or machine washable, is reusable, and is reversible.

(g) To provide a digital padding device with a tubular elastic fabric member which resists fraying without the necessity of employing time-consuming, expensive, and awkward antifraying measures by using a seamless elastic tubular material which will spontaneously roll inward at the ends of the pad to form a cuff.

Further objects and advantages of my invention will become apparent from a consideration of drawings and ensuing descriptions of the same.

BRIEF DESCRIPTIONS OF THE DRAWINGS

DESCRIPTION OF THE INVENTION

Figure 1:
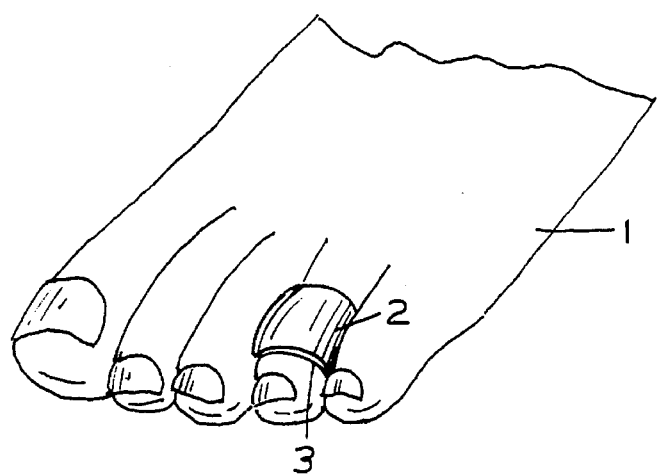
FIG. 1 is a perspective view of a corn pad of the present invention positioned on the fourth toe of a foot.
Figure 2:
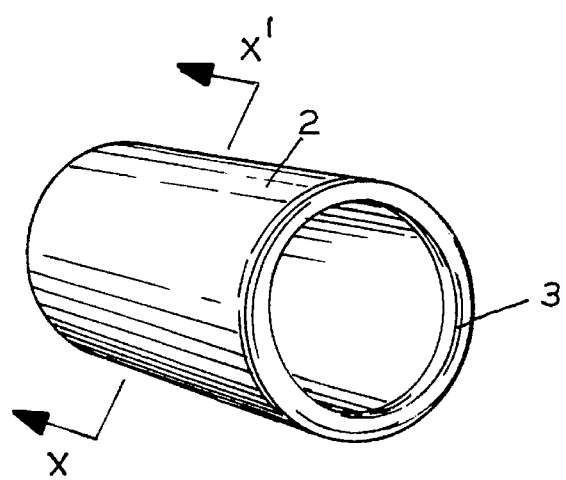
FIG. 2 is a perspective view of a corn pad of the present invention illustrating the elastic tube structure and the rim or cuff of the tube.
Figure 3:
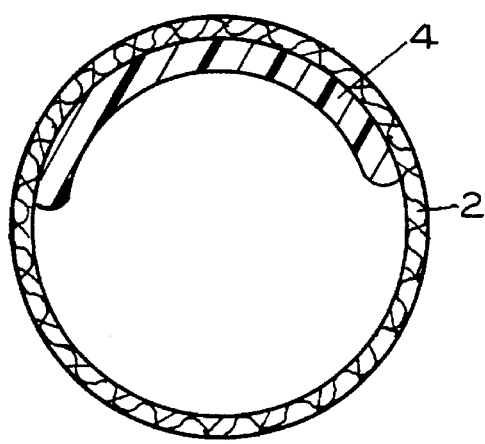
FIG. 3 is a sectional view of the corn pad pictured in FIG. 2 taken at line X—X$^1$ and illustrating a viscoelastic gel of uniform thickness impregnated on the interior of the elastic sleeve.
Figure 4:
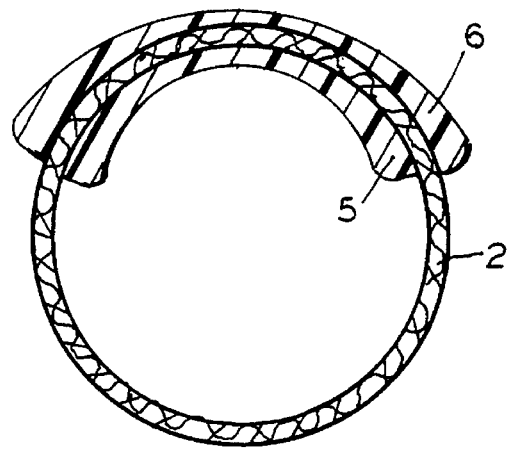
FIG. 4 is a sectional view of a corn pad of the present invention illustrating gel pads of variable thickness positioned on both the interior and exterior surfaces of the elastic tube.

FIGS. 1–4 illustrate one preferred embodiment of the present invention which in its simplest form comprises only two components, a sleeve of elastic fabric 2 and a pad(s) of viscoelastic gel 4, 5, 6 impregnated thereupon. FIG. 1 illustrates a corn pad of the present invention that has been applied to a toe. The elastic sleeve 2 encircles the digit and holds the viscoelastic gel in direct contact with the corn or other lesion. FIG. 2 illustrates the elastic sleeve 2 of a corn pad of the present invention and shows the cuff 3 formed around the rim of sleeve 2 by the inward rolling of the elastic fabric. FIG. 3 is a cross-sectional view of the embodiment of the present invention shown in FIG. 2 to illustrate the location of a layer of uniform thickness of viscoelastic gel 2, specifically on the interior aspect of the elastic sleeve 2. This configuration allows for the oleaginous gel 4 to come into direct contact with the corn or other lesion to facilitate softening and lubrication of the corn with the plasticizing oil of the gel. This configuration also enhances the gel's ability to freely conform to an uneven surface without hindrance from a sheet of material that might be used to cover the gel. In FIG. 3, the layer of viscoelastic gel is of essentially uniform thickness. FIG. 4 illustrates one embodiment of the present invention wherein the layers of gel 5, 6 have a variable thickness. In FIG. 4 the surface of the gel 5 intended for contact with the skin is depicted a concave in shape to better adapt to the convexity of a corn or hammertoe, for example. The gel pad or pads of the corn pad thus may be of uniform thickness, variable thickness, or even zero thickness where an aperture is desirable.

Figure 5:
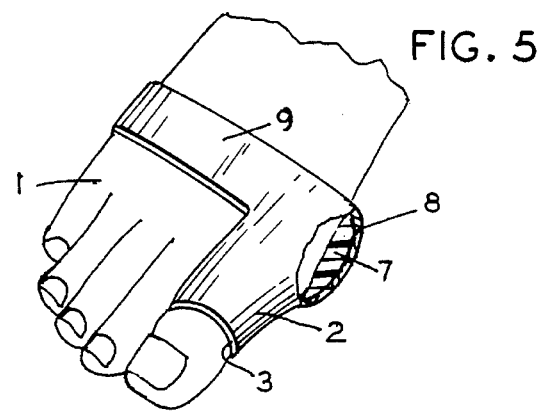
FIG. 5 is a perspective view of a bunion pad of the present invention positioned on a foot with the aid of a metatarsal encircling strap.

The manufacture of the present invention as illustrated in FIGS. 1–4 is extremely simple. My technique involves purchasing a commercially available tubular sleeve of elastic fabric; flattening this elastic fabric on a level surface such as a workbench; laying circular molds on the fabric; and pouring heated, liquefied polymer directly into the mold and allowing it to cool and re-gel. For my prototypes, I have been using a seamless tube of elastic fabric from ½" to 2" in diameter available from Surgical Appliance Industries of Cincinnati, Ohio. The advantage that I have found with this particular knit is that it resists fraying around the rims by spontaneously rolling up at the rims to form a cuff 3 (FIG. 2) at either end as described in greater detail subsequently in this disclosure. After flattening this elastic fabric tube on a level working surface, I place the gel molds directly on the surface of the fabric where the gel is to be deposited. For gel molds I have been using rubber washers of varying diameters and thicknesses. Such rubber washers are readily available at most hardware or plumbing stores. These washers are simply laid on the fabric with no need to secure them in the desired position. Next, I take some commercially available viscoelastic gel such as the thermoplastic gelatinous composition taught by Chen in U.S. Pat. No. 4,369,184 and sold under the name of Glue-Balls® by Hymen Products and heat these in a saucepan on an electric stove. Once the gel has been heated to around 350° F. and converted to a free-flowing liquid, I simply pour a small portion of the liquefied polymer into the mold and allow it to cool and re-gel. Once the hot, liquefied gel is in the mold, it begins to penetrate the elastic fabric and is partially absorbed by the fabric. Upon cooling and re-jelling of the polymer, the viscoelastic gel becomes intimately bonded to the fabric. After the polymer has cooled and re-jelled, the molds are simply lifted off of the fabric and the impregnation of the fabric with the gel is complete. The next step involves simply cutting the fabric between consecutive gel pads, dusting the gel with talc, and turning the short tube segments inside out so that the gel pad resides on the interior aspect of the finished device. When using the above-mentioned tubular knit manufactured by Surgical Appliance Industries, no elaborate means such as applying an antifraying substance to the cut edges of the elastic fabric are required to achieve a reusable, washable, and reversible device that will not fray at the ends. Another advantage of this extremely simple method of manufacture is that no costly injection molding procedure or equipment is required. In order to obtain a gel pad of variable thickness, as illustrated in FIGS. 4 and 5, several simple steps can be employed. The method I prefer involves pouring the liquefied gel into the mold and letting it cool to approximately its gelling temperature. At this point, the gel is still moldable, somewhat like putty. I take a rubber ball coated with talc and press it down on the exposed surface of the gel. This "stamps" the gel into the desired shape. Obviously, modifications of this basic concept could be made to facilitate mass production. Another technique I have employed to achieve a varied thickness to the gel involves laying a small object such as a coin under the fabric to be coated with gel such that the fabric becomes elevated and reduces the distance between the surface of the fabric and the top surface of the mold.

Figure 7:
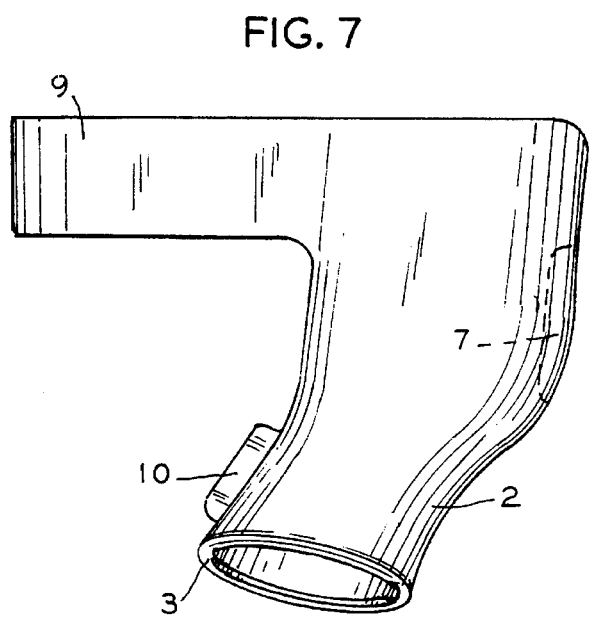
FIG. 7 is a perspective view of a bunion pad of the present invention with a metatarsal encircling elastic band and a viscoelastic gel pad positioned on the lateral external surface of the digital sleeve.
Figure 5A:
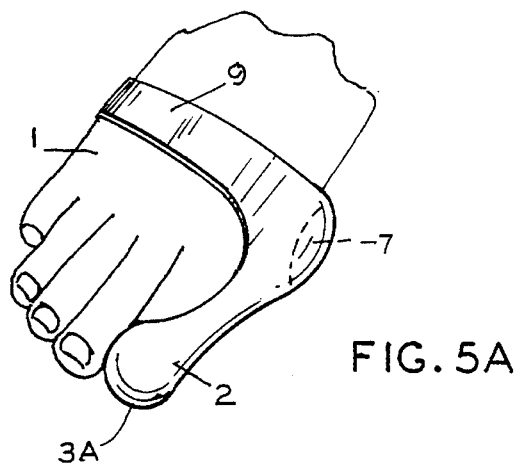
FIG. 5A is a variation on the bunion pad illustrated in FIG. 5, but with the distal aspect of the elastic tube structure closed.
Figure 6:
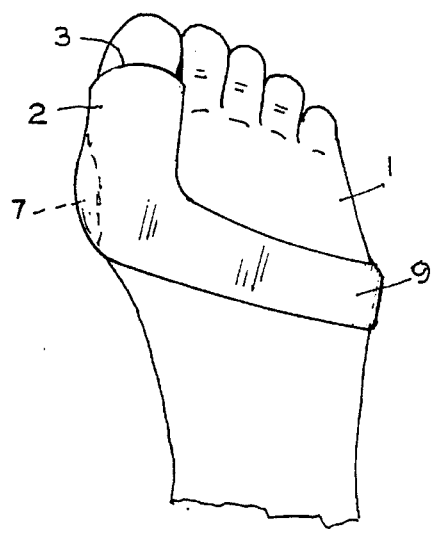
FIG. 6 is a plantar view of the bunion pad of the present invention illustrated in FIG. 5, affixed to a foot.
Figure 8:
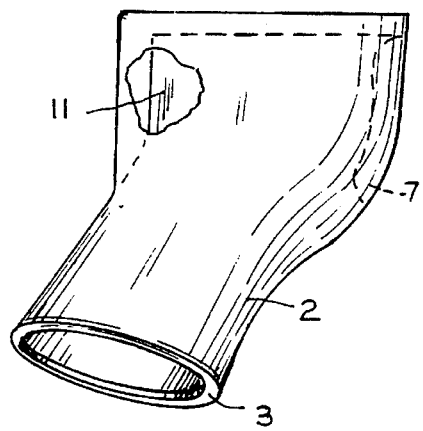
FIG. 8 is a perspective view of a bunion pad of the present invention without a metatarsal encircling band.

FIGS. 5–8 illustrate a bunion pad of the present invention. FIG. 5 depicts one embodiment of the invention wherein a digit encircling elastic tube 2 is applied to the hallux to anchor the distal aspect of the bunion pad. As with the corn pad depicted in FIG. 3, the distal rim of the device is a cuff 3 (FIGS. 5–8) formed by the inward rolling of the elastic fabric sleeve 2. Alternatively, as illustrated in FIG. 5A, the distal end of elastic tube 2 may be closed 3A. In this case the elastic fabric tube forms a "sling" that fits over the distal aspect of the digit to anchor the device against proximal migration. The proximal medial segment of the bunion pad 8 is made of elastic fabric which covers the dorsal aspect of the first metatarsophalangeal joint, wraps around the medial aspect of the joint, and covers the plantar aspect of the first metatarsophalangeal joint as illustrated in FIGS. 5 and 6. A metatarsal encircling elastic strap 9 (FIGS. 5–7) connects with the proximal dorsal aspect of the proximal segment 8 of the bunion pad, courses dorsally over the metatarsus of the foot 1, wraps around the fifth metatarsal proximal to the fifth metatarsal head, courses across the plantar metatarsus, and connects with the plantar proximal-lateral aspect of the proximal aspect 8 of the bunion pad. A pad of viscoelastic gel 7 is impregnated on the interior aspect of the device in a location corresponding to the roedial aspect of the first metatarsophalangeal joint. Gel pad 7 may be of uniform thickness, variable thickness, or even zero thickness when an aperture is desired. One embodiment of the invention employs a gel pad with a central concave depression to interface with the convexity of a bunion. Referring to FIG. 7, an optional gel pad 10 may be impregnated onto the external lateral surface of the hallux encircling segment 2 of the device. Pad 10 functions as a toe spacer between the first and second digits. Pad 10 could just as well be impregnated onto the interior surface of sleeve 2. Referring to FIG. 8, an alternative embodiment of a bunion pad of the present invention is illustrated. Structures 2, 3, and 7 are substantially as described for the embodiment depicted in FIGS. 5–7. The primary difference between the bunion pad illustrated in FIG. 8 and the bunion pads illustrated in FIGS. 5–7 is that the bunion pad in FIG. 8 lacks the metatarsal encircling elastic strap 9. The elastic fabric may be reinforced with a rigid or semi-rigid backing structure in this embodiment so that gel pad 7 is retained in its most advantageous position relative to the bunion. The plantar proximal aspect 11 of the devise is indicated by the dotted line in FIG. 8.

My method for manufacturing the bunion pad of the present invention is as follows. Beginning with an approximately 3-inch segment of elastic tubular fabric (Surgical Appliance Industries, Cincinnati, Ohio) a pad of viscoelastic gel is impregnated on one surface using the same technique as described above for the corn pad of the present invention. This pad is substantially in the center of the longitudinal axis of the elastic sleeve. After the gel has cooled, the sleeve of elastic fabric is inverted such that the gel pad is on the interior surface of the elastic sleeve. Using ordinary scissors, a cut is made longitudinally for approximately three-fourths the length of the elastic sleeve on the opposite side of the sleeve as the viscoelastic gel. The resultant device is now substantially the same as the embodiment pictured in FIG. 8. Next, a segment of elastic strap material approximately 4–6 inches long is sewn onto the device at the proximal aspects of the elastic tubular material where the longitudinal cut was begun. One end of the elastic strap is sewn to the dorsal proximal aspect of the device and the other end of the elastic strap is sewn onto the plantar proximal aspect of the device. This results in the bunion pad illustrated in FIGS. 5 and 6. An optional gel pad may be impregnated onto either the exterior or interior surface of the bunion pad at the distal aspect as illustrated by 10 (FIG. 7). This substantially results in the finished product ready for use.

OPERATION OF THE INVENTION

The corn pad of the present invention is practiced by simply slipping the elastic tubular member over the digit. The viscoelastic gel pad can be positioned by rotating the elastic fabric and by pulling the elastic fabric carrier structure proximally or distally on the digit. Since the elastic fabric will naturally apply slight pressure on the extremely deformable viscoelastic gel in the direction of the digit, the gel will spontaneously assume the surface configuration of the lesion being treated, thus eliminating the need to modify the shape of the pad during manufacture. Since this viscoelastic gel behaves like a fluid when pressure is applied, this pressure will be more equally dissipated throughout the gel in a "hydraulic" manner similar to the way pressure is dissipated through the breaking system of an automobile when pressure is applied to the brake pedal. In response to the pressure, the ultraconformable, noncompressible, viscoelastic gel will "flow" over the surface being treated and fill in voids in the surface so as to equalize pressure over the surface being treated in a manner far superior to conventionally-used materials such as compressible felt or foam rubber. When pressure is applied to the noncompressible viscoelastic gel, it will "flatten out" by expanding its radius or surface area. Thus, the applied pressure will be spread out over a greater area with less pressure per unit of area.

When frictional or horizontal shearing forces are applied to the invention, this force is internally absorbed by the gel without the gel pad sliding forward and backward on the digit. These results cannot be duplicated in prior inventions known to the art of pads for corns, calluses, bunions, blisters, and the like, because of the unique properties of the gel of the present invention. Gels heretofore known to the art of orthopedic padding devices have such limited elasticity and such poor tearing parameters that they will usually split into two or more pieces when stretched to about twice their resting length. This inability to elongate to many times its original length thus impedes the ability of these gels to flow in response to pressure or frictional forces. When using a gel such as described by Chen in U.S. Pat. No. 4,369,284 in the present invention, new and unexpected results are discovered. The most significant of these results from a clinical standpoint is the tremendous amount of frictional or shearing forces that can be absorbed by a relatively thin layer of such a gel. The aforementioned gel of Chen is capable of being stretched to 1600% of its original length before tearing. For the sake of illustration, one can imagine a pad of the present invention with a 2.0 mm thick pad of such a material. When a shearing force is applied parallel to a major surface of this hypothetical 2.0 mm gel pad, this surface is displaced laterally while the elastic gel stretches. A 2.0 mm thick pad of such a material could thus be displaced 2.0 mm ×16, or nearly 32 mm (1 and ¼ inch) in one direction. By reversing this shearing force 180°, the gel will return to its resting point and then begin stretching in the opposite direction an equal distance. The total range of motion in this hypothetical case would thus be 1.25 inches ×2 or 2.5 inches. One can see in this example the superior friction dissipating ability that one can realize when using a thin layer of such a material-an important consideration in the narrow confines of a shoe. The above discussion is presented to better illustrate the direct relationship between gel elasticity and shear dissipating ability. In real-life situations the results may vary. Nonetheless, it seems reasonable that if one particular gel pad was capable of being elongated four times as much as a second gel pad, the first gel pad could absorb approximately the same amount of shearing force as the second gel pad when the first gel pad is only one-fourth the thickness of the second gel pad. This economy of space is submitted to be a significant breakthrough when compared to the prior art. Therefore, for the purposes of the present invention, only viscoelastic gels capable of elongating to at least 200% of their original length without tearing are considered as compatible with the present invention.

An analogous argument can be constructed to illustrate the superior pressure dissipating ability of such gels in the present invention. In the case of force applied perpendicular to the major surface of a gel of the present invention, such pressure is dissipated by the flow of the gel radially outward from an area of higher pressure to an area of lower pressure. Likewise, it seems reasonable in this case that a gel that can easily elongate to many times its original resting length would do a better job of dissipating pressure in an hydraulic manner.

When the invention is applied over the dry, compacted keratin in a corn, for example, plasticizing oil such as Mineral Oil U.S.P. will be transferred from the gel to the keratotic lesion to soften and lubricate the lesion. Medications incorporated into the gel will likewise be delivered to this superficial lesion.

When utilizing an elastic fabric tube made from material such as described above, no expensive, time-consuming, or elaborate measures to prevent fraying of the fabric are required because the cut edges of the elastic tube will spontaneously roll up to form a fray-proof "cuff."

When the corn pad of the present invention becomes soiled, it can simply be removed and machine-washed and dried. I have subjected prototypes of the invention to several cycles of washing and drying without any noticeable change in their ability to function as described above. When desirable, the elastic fabric sleeve can be turned inside out so that the gel resides on the external surface of the tube. In one embodiment of the invention, gel pads are deposited on both surfaces of the elastic tube opposite each other. With this device, one can position the pads between two adjacent toes to function as a toe spacer that will help realign the digits. This is an important function for people suffering from hallux abductovalgus or bunion formation where the great toe deviates away from the midline of the body and presses into the adjacent toes.

The operation of the bunion pad of the present invention is similar to that of the corn pad. To apply the bunion pad illustrated in FIG. 8, the distal tubular member 2 is simply slipped over the digit so that the gel pad 7 is positioned over the medial aspect of the first metatarsophalangeal joint (or over the lateral aspect of the fifth metatarsophalangeal joint in the case of a tailor's bunion). When applying the embodiment of the bunion pad illustrated in FIGS. 5–7, the elastic strap 9 is first pulled over the metatarsus of the foot. Next the digit (either hallux or little toe) is slipped into the distal tubular aspect 2 of the device. This device positions the gel pad over or around a bunion where it can gently apply lateral pressure to realign a splayed first or fifth metatarsal. The proximal pull of elastic fabric is transmitted to the digit encircling sleeve in such a manner as to realign a deviated metatarsophalangeal joint.

To better understand the operation of the present invention, the following discussion of the more salient features of the present invention is submitted. My invention is fundamentally different from the prior art because it takes advantage of the unique properties of a noncompressible, relatively fluid, highly comformable, viscoelastic gel to overcome the inability of previously described pads to dissipate localized points of pressure created against the foot when wearing shoes. In the parent applications, I describe this ability of certain viscoelastic polymers to flow around an uneven surface when pressure is applied in such a manner as to equalize the pressure throughout the area as "hydraulic" in nature and similar to the way in which "hydraulic fluid distributes pressure equally in all directions in a pump or brake device." When ultrasoft, highly conformable, noncompressible viscoelastic gels are used according to the method taught in this patent application, this is precisely the case. The materials that I have been working with are exemplified by the thermoplastic elastomer gelatinous compositions taught by Chen in U.S. Pat. No. 4,369,284. If one were to take a cylinder 3" in diameter and ½" in height, for example, and made of felt, foam rubber, or any of the other materials described in this art and were to step on it with a bare foot, what would happen is that these compressible materials would decrease in volume and increase in density. In those areas where pressure form the foot were greatest, the material would be the densest and least able to cushion. This compacted material would also lose its limited ability to absorb horizontal shearing of frictional forces such as found when walking with a shoe on. Such a pad would not appreciably expand or spread outwardly in a radial manner in such a way as to increase the surface area of contact between the foot and the pad and thus dissipate the force over a larger area. When a noncompressible viscoelastic gel of the same dimensions is utilized in place of the compressible padding material, the results are quite different. As force is exerted downward on the ultrasoft, highly deformable, noncompressible gel, it instantly begins to flow radially outward in a manner which greatly increases the surface area of contact between the gel and the foot. This increased surface area dissipates the weight over a larger area, resulting in a lower pressure per unit of area. This force tending to spread out the gel is opposed by the intrinsic elastic properties of the viscoelastic gel, and this spreading will cease when these two forces are in equilibrium. Likewise, there will be no discrete pressure points found within the gel due to the unequal pressure applied by the irregularly-shaped foot. In those areas where pressure would build up in the conventional pad, the gel will flow radially outward and dissipate this pressure throughout the system in a "hydraulic" manner which is far superior to the way that pressure is dissipated in a noncompressible material. Unlike materials heretofore used in this art, a viscoelastic gel will not lose its ability to internally absorb frictional or horizontal shearing forces when subjected to pressure. In fact, the ability of these types of gels to internally absorb these horizontal shearing forces when subjected to pressure is so great as to render them unsuitable for use as insoles unless incorporated into a system that restricts this tendency to slide horizontally. This is an important consideration when discussing pads for corns, bunions, and especially blisters because much of the pain and inflammation resulting from these conditions is the result of friction between the foot and the shoe that is generated during walking as the foot slides forward and backward inside the shoe.

There are several difficult and subtle problems that must be recognized and solved when incorporating a highly deformable, ultrasoft, noncompressible, viscoelastic gel into a pad for corns, hammertoes, bunions, and the like. The first problem relates to the tendency for gels to migrate away from an area of increased pressure, especially when this is an intermittent pressure such as found inside a shoe when walking. This repeated pumping action would cause an unsecured gel to be squeezed away from the area of high pressure to an area of lower pressure. The present invention solves this problem by directly impregnating a thermoplastic viscoelastic gel onto fabric. This is accomplished by heating the gel to a temperature that converts it to a free-flowing liquid. This hot liquid is then poured onto a fabric and allowed to cool and re-gel. While in the heated-liquid state, the viscoelastic polymer will penetrate the fabric, be partially absorbed by it, and bond to the fabric when it cools and returns to the gel state. This impregnation process serves to bond the gel to the fabric so that the fabric can prevent the gel from excessive migration when pressure is applied. Even though the gel may be highly stretchable, it will not be able to travel far when the gel is applied in a layer less than 1.0 cm thick. Thus, the fabric "tethers" the gel to prevent unlimited migration. The second problem encountered when devising a pad for corns, hammertoes, and the like using a viscoelastic gel is related to the above first said problem and is actually the converse of it. Ideally, one would like to create a system that prevents excessive and unlimited migration of the gel but, at the same time, facilitates the limited type of gel migration required to maximize the equilibration of pressure throughout the gel. One would also want to avoid a gel-fabric system that would allow a portion of the gel to be squeezed out of the pad where it can become entangled in the sock. These objectives are best satisfied by utilizing a two-way stretchable elastic fabric such as Spandex®. Since such a fabric is itself elastic, it will stretch a limited amount with the gel in response to an increase in localized pressure to facilitate the dissipation of this pressure and better equalize the pressure in the gel-fabric system. As the gel expands radially outward in response to pressure, so too does the fabric. Thus, the viscoelastic gel and the elastic fabric work synergistically to equalize the dissipate pressure over a larger area of the foot. This also prevents the gel from being squeezed out of a cleft between the fabric and the skin which could cause the gel to be pulled away from the pad when socks are applied or removed because of the sliding frictional force applied to the gel as the sock is pulled on or off. This is one problem I have encountered utilizing viscoelastic gel with nonelastic fabrics. A third and related problem encountered when utilizing viscoelastic gels in this art is their floppy nature and tendency to roll up into an amorphous ball of gel in response to horizontal frictional forces such as encountered when putting on a sock or walking in a shoe. For this reason, it is important that the entire surface of the gel be either in contact with the skin or covered with a sheet of fabric that secures the entire mass of the gel to the body part being treated by applying force in the direction of said body part. This is why I have chosen the elastic tube structure for this invention which is intended for use on a human digit which is cylindrical in shape. The relationship between the elastic fabric and the viscoelastic gel is very similar to the relationship between skin and fat in the mammal. Skin essentially is a two-way stretch elastic covering for subcutaneous fat which pads in a manner exactly the same as the viscoelastic gel of the present invention. The elastic fabric tube will apply even compression to the entire surface of the gel that is not in contact with the skin and thus eliminate any unsecured extension of the gel which would roll up in response to friction such as found when applying a sock.

Thus, the reader will see that the present invention is a highly-useful and novel device for padding and medicating corns, calluses, bunions, blisters, hammertoes, and the like. The invention dissipates the pressure and friction exerted upon the foot by a shoe when walking in a manner far superior to any device known to this art. The present invention is further capable of lubricating, softening, moisturizing, and medicating foot lesions in a manner heretofore not known to the art. The present invention is an orthopedic padding device that self-conforms to the shape of a foot lesion without the need to preshape the gel pad during manufacture; internally absorbs horizontal shearing or frictional forces; is easy to apply and remove; dissipates the elastic compressive forces utilized to hold it in place over a larger surface area so as not to interfere with circulation to the digit; and is machine washable, reversible, and reusable.

While the above description contains many specificities, these should not be construed as limitations on the scope of the invention, but rather as an exemplification of several preferred embodiments thereof. For example, materials which do not match the specific definition of a "gel" but which have equivalent physical properties such as a highly deformable, ultrasoft, noncompressible, viscoelastic rubbery material such as may be formulated using silicone or other such materials could be substituted into the present invention. Likewise, materials with similar physical properties which are not thermoplastic could be utilized to achieve the same results as the gel in the present invention. For example, a multipart chemical material which "sets up" or cures after mixing could be impregnated onto the elastic tubular means of the present invention with equivalent results. Also, a physically similar compound that cures upon exposure to air or heat could be utilized in the present invention. Furthermore, it is to be understood that this device is as easily adapted to treat a fifth metatarsophalangeal (or tailor's) bunion as it is the hallux abductovalgus-type bunion.

I claim:

1. A padding device for the human foot, comprising:

a. a tubular sleeve of elastic fabric fitting about a digit and having an inside surface, an outside surface and opposing ends;

b. said tubular sleeve of elastic fabric being formed of a seamless tubular material which spontaneously rolls inwards about each end of said tubular sleeve to form a cuff thereat; and c. a pad of viscoelastic gel;

d. said pad of viscoelastic gel being directly impregnated onto said inside surface of said tubular sleeve of elastic fabric.

2. The padding device, as recited in claim 1, where the viscoelastic gel includes plasticizing oil in the form of Mineral Oil U.S.P.

3. The padding device, as recited in claim 2, where the plasticizing oil is perfused with an oil soluble medicinal agent.

4. The padding device, as recited in claim 1, wherein said pad of viscoelastic gel is capable of being stretched at least 200 percent of any resting dimension without tearing.

5. The padding device, as recited in claim 1, wherein the viscoelastic gel is thermoplastic in nature.

6. The padding device, as recited in claim 1, wherein, additionally, there is a second pad of viscoelastic gel which is impregnated directly upon the outside surface of said tubular sleeve.

7. The padding device, as recited in claim 1, wherein the pad of viscoelastic gel is of uniform thickness.

8. The padding device, as recited in claim 1, wherein the pad of viscoelastic gel varies in thickness.

9. A padding device for the human foot, comprising:

a. an elastic fabric member having a portion in the form of a tubular sleeve to encircle a digit of the human foot and a non-tubular portion which extends from said digit encircling tubular sleeve to lie adjacent to a metatarsophalangeal joint associated with said digit;

b. said tubular sleeve portion of said elastic fabric member being closed at the distal end so as to encompass the distal end of said digit to prevent migration of the padding device; and c. a pad of viscoelastic gel;

d. said pad of viscoelastic gel being directly impregnated onto said non-tubular portion of said elastic fabric member so as to be positioned adjacent to said metatarsophalangeal joint.

10. The padding device, as recited in claim 9 above, wherein, additionally, an elongated strap of elastic fabric is attached to said non-tubular portion of said elastic fabric member, said elongated strap of elastic fabric being formed to encircle the metatarsal region of the human foot.

11. The padding device, as recited in claim 9 above, where said pad of viscolastic gel varies in thickness.

12. The padding device, as recited in claim 9, wherein said viscoelastic gel includes Mineral Oil U.S.P. as a plasticizer.

13. The padding device, as recited in claim 12, wherein said plasticizer includes an oil soluble medicinal agent.

14. The padding device, as recited in claim 9, wherein said viscoelastic gel is thermoplastic.

15. The padding device, as recited in claim 9, wherein said pad of viscoelastic gel is capable of being stretched at least 200 percent of any resting dimension without tearing.

16. A padding device for the human foot, comprising:

a. an elastic fabric member having a portion in the form of a tubular sleeve to encircle a digit of the human foot and a non-tubular portion which extends from said digit encircling tubular sleeve to lie adjacent to a metatarsophalangeal joint associated with said digit; said tubular sleeve having an inside surface and an outside surface;

b. a first pad of viscoelastic gel being directly impregnated onto said non-tubular portion of said elastic fabric member so as to be positioned adjacent to said metatarsophalangeal joint; and c. a second pad of viscoelastic gel which is directly impregnated upon said outside surface of said tubular sleeve encircling said digit so as to lie between, and separate, said digit and a second, adjacent digit.

* * * * *